(12) United States Patent (10) Patent No.: US 12,626,810 B2

Jikuhara et al. (45) Date of Patent: May 12, 2026

(54) SERVER APPARATUS, SYSTEM, AND OPERATING METHOD OF SYSTEM

(71) Applicant: TOYOTA JIDOSHA KABUSHIKI KAISHA, Toyota (JP)

(72) Inventors: Yoshikazu Jikuhara, Miyoshi (JP); Seii Sai, Yokohama (JP); Ibuki Shimada, Miyoshi (JP); Takahiro Aoki, Saitama (JP); Keishi Kinoshita, Tokyo-to (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 395 days.

(21) Appl. No.: 18/322,888

(22) Filed: May 24, 2023

(65) Prior Publication Data

US 2023/0386654 A1      Nov. 30, 2023

(30) Foreign Application Priority Data

May 25, 2022      (JP) ................................. 2022-085149

(51) Int. Cl.
| | |
|---|---|
| *G16H 40/20* | (2018.01) |
| *G01C 21/20* | (2006.01) |
| *G16H 10/60* | (2018.01) |
| *G16H 40/67* | (2018.01) |

(52) U.S. Cl.
CPC ............. *G16H 40/20* (2018.01); *G01C 21/20* (2013.01); *G16H 10/60* (2018.01); *G16H 40/67* (2018.01)

(58) Field of Classification Search
CPC ........ G16H 40/20; G16H 10/60; G16H 40/67; G16H 40/63; G16H 50/30; G01C 21/20; G01C 21/3438; H04L 67/12; H04L 67/125; H04L 67/51; H04L 67/52; G08G 1/096833
See application file for complete search history.

(56) References Cited

U.S. PATENT DOCUMENTS

| | | | | |
|---|---|---|---|---|
| 6,117,073 | A * | 9/2000 | Jones | G16H 50/20 |
| | | | | 600/300 |
| 10,303,851 | B2 * | 5/2019 | Nguyen | G16H 20/17 |
| 10,696,397 | B2 * | 6/2020 | Sekine | G05D 1/0011 |
| 10,909,985 | B1 * | 2/2021 | Whittenburg | G10L 15/30 |
| 11,694,791 | B2 * | 7/2023 | Hara | G06Q 10/1093 |
| | | | | 701/23 |
| 11,780,473 | B2 * | 10/2023 | Ota | A61B 5/1077 |
| | | | | 701/23 |
| 12,089,966 | B1 * | 9/2024 | McNair | A61B 5/7275 |

(Continued)

FOREIGN PATENT DOCUMENTS

| | | |
|---|---|---|
| JP | 2021022332 A | 2/2021 |

*Primary Examiner* — Mamon Obeid

(74) *Attorney, Agent, or Firm* — Dickinson Wright, PLLC

(57) ABSTRACT

A server apparatus includes a communication interface and a controller configured to communicate using the communication interface. The controller is configured to receive information for identifying a patient from a terminal apparatus and output, on a condition that a total examination time is equal to or less than a travel time for a travel route of the patient, information to one or more medical examination vehicles that each provide a medical examination for one or more examination items on which the patient has not yet been examined, the information being for causing the one or more medical examination vehicles to travel the travel route.

18 Claims, 6 Drawing Sheets

(56)    References Cited

U.S. PATENT DOCUMENTS

| | | | |
|---|---|---|---|
| 2004/0201239 A1* | 10/2004 | Pellegrin, Jr. | A61G 3/001 |
| | | | 296/24.38 |
| 2005/0060198 A1* | 3/2005 | Bayne | G16H 10/60 |
| | | | 705/2 |
| 2005/0240613 A1* | 10/2005 | Logan | G06Q 50/22 |
| | | | 707/999.102 |
| 2008/0033752 A1* | 2/2008 | Rodgers | G16Z 99/00 |
| | | | 705/2 |
| 2008/0287746 A1* | 11/2008 | Reisman | G16H 40/63 |
| | | | 600/300 |
| 2011/0074585 A1* | 3/2011 | Harmon | G06Q 10/087 |
| | | | 715/738 |
| 2015/0025329 A1* | 1/2015 | Amarasingham | A61B 5/0022 |
| | | | 600/300 |
| 2016/0027138 A1* | 1/2016 | Larsen | G06F 21/31 |
| | | | 705/2 |
| 2017/0140119 A1* | 5/2017 | Laha | G16Z 99/00 |
| 2017/0308648 A1* | 10/2017 | Clarke | G16H 10/60 |
| 2018/0315298 A1* | 11/2018 | Kitamura | G08B 25/08 |
| 2019/0197438 A1* | 6/2019 | Meredith | G08G 1/096811 |
| 2020/0365263 A1* | 11/2020 | Kobayashi | G01C 21/206 |
| 2020/0381094 A1* | 12/2020 | Myers | G06F 1/163 |
| 2021/0035038 A1 | 2/2021 | Suzuki et al. | |
| 2021/0061314 A1* | 3/2021 | Hara | G08G 1/127 |
| 2021/0090729 A1* | 3/2021 | Murphy | G16H 40/67 |
| 2021/0380126 A1* | 12/2021 | Liu | G06N 5/02 |
| 2023/0083724 A1* | 3/2023 | Cella | G06F 16/24537 |
| | | | 705/28 |
| 2023/0252382 A1* | 8/2023 | Simpson | G06Q 50/02 |
| | | | 701/410 |
| 2023/0274211 A1* | 8/2023 | Jikuhara | G08G 1/096844 |
| | | | 705/7.25 |
| 2023/0274825 A1* | 8/2023 | Jikuhara | G06F 21/6245 |
| | | | 705/2 |
| 2023/0352158 A1* | 11/2023 | Jikuhara | G16H 40/67 |
| 2024/0005797 A1* | 1/2024 | Jikuhara | G16H 40/20 |
| 2024/0203545 A1* | 6/2024 | Chung | G16H 50/20 |

* cited by examiner

1

SERVER APPARATUS, SYSTEM, AND OPERATING METHOD OF SYSTEM

CROSS-REFERENCE TO RELATED APPLICATION

This application claims priority to Japanese Patent Application No. 2022-085149, filed on May 25, 2022, the entire contents of which are incorporated herein by reference.

TECHNICAL FIELD

The present disclosure relates to a server apparatus, a system, and an operating method of a system.

BACKGROUND

In recent years, various services have been implemented using means of transportation such as vehicles. One such technology, for example, has been proposed to support users undergoing medical examinations in a circulating vehicle equipped with facilities for providing medical examinations (Patent Literature 1).

CITATION LIST

Patent Literature

PTL 1: JP 2021-022332 A

SUMMARY

Services that provide medical examinations by vehicle have room for improvement in user convenience.

In view of the above, a server apparatus and the like for managing medical examination vehicles that can improve user convenience are disclosed below.

A server apparatus according to the present disclosure includes:

a communication interface; and a controller configured to communicate using the communication interface, wherein the controller is configured to receive information for identifying a patient from a terminal apparatus and output, on a condition that a total examination time is equal to or less than a travel time for a travel route of the patient, information to one or more medical examination vehicles that each provide a medical examination for one or more examination items on which the patient has not yet been examined, the information being for causing the one or more medical examination vehicles to travel the travel route.

A system according to the present disclosure includes one or more medical examination vehicles and a server apparatus configured to communicate with each other, wherein the server apparatus is configured to receive information for identifying a patient from a terminal apparatus and output, on a condition that a total examination time is equal to or less than a travel time for a travel route of the patient, information to the one or more medical examination vehicles that each provide a medical examination for one or more examination items on which the patient has not yet been examined, the information being for causing the one or more medical examination vehicles to travel the travel route, and

2 the one or more medical examination vehicles are configured to travel the travel route based on the information from the server apparatus.

An operating method of a system according to the present disclosure is an operating method of a system including one or more medical examination vehicles and a server apparatus configured to communicate with each other, the operating method including:

receiving, by the server apparatus, information for identifying a patient from a terminal apparatus and outputting, on a condition that a total examination time is equal to or less than a travel time for a travel route of the patient, information to the one or more medical examination vehicles that each provide a medical examination for one or more examination items on which the patient has not yet been examined, the information being for causing the one or more medical examination vehicles to travel the travel route; and traveling, by the one or more medical examination vehicles, the travel route based on the information from the server apparatus.

According to server apparatus and the like in the present disclosure, medical examination vehicles can be managed in a way that contributes to improving user convenience.

DETAILED DESCRIPTION

Embodiments are described below.

Figure 1:
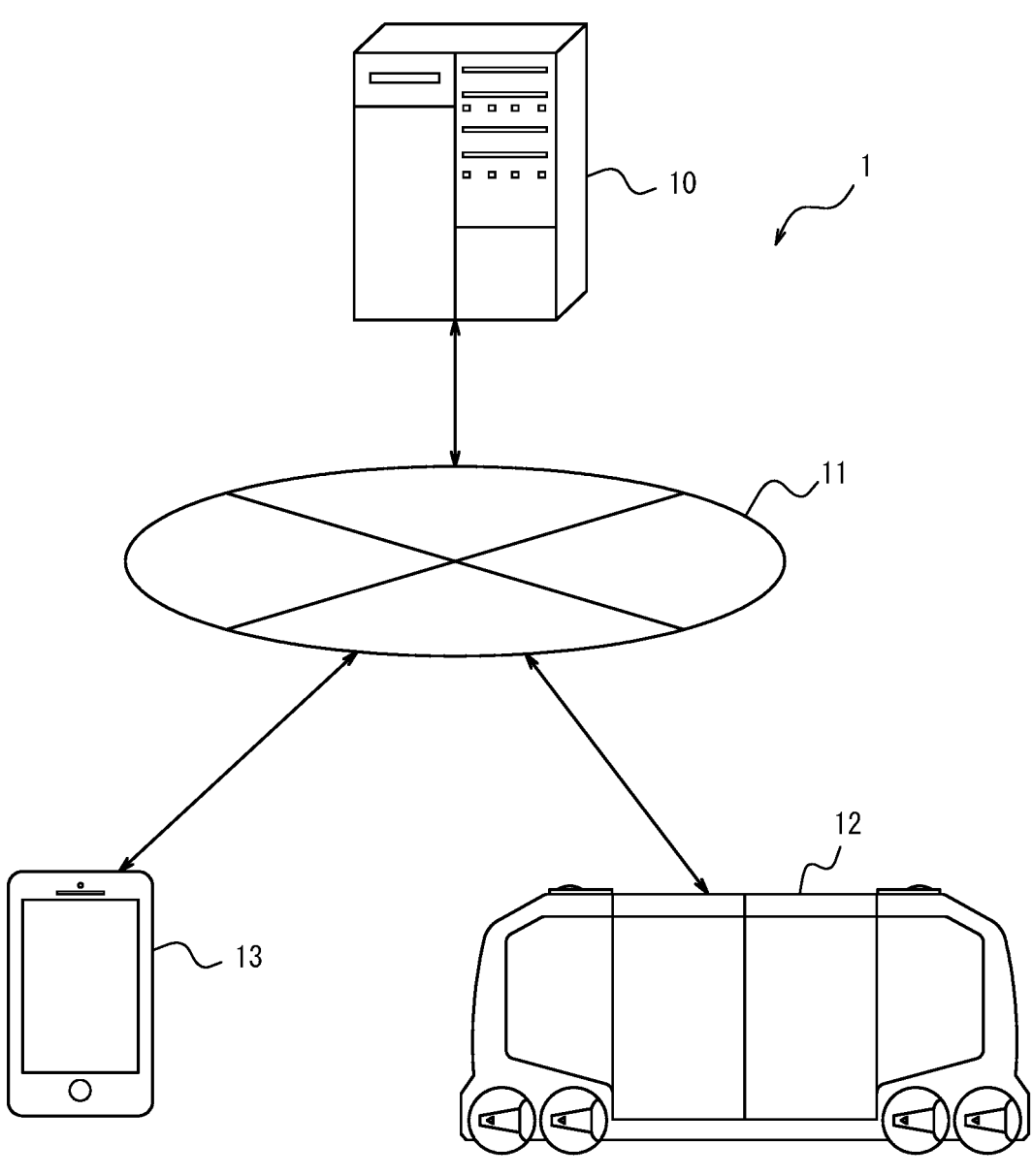
FIG. 1 is a diagram illustrating an example configuration of an information processing system.

FIG. 1 is a diagram illustrating a configuration example of an information processing system according to an embodiment. An information processing system 1 includes one or more each of a server apparatus 10, a medical examination vehicle 12, and a terminal apparatus 13 communicably connected to each other via a network 11.

The server apparatus 10 is, for example, a server computer that belongs to a cloud computing system or other computing system and functions as a server that implements various functions.

The medical examination vehicle 12 is equipped with medical examination equipment to perform one or more examination items in a medical examination. The examination items include, for example, body measurements, blood pressure measurement, blood composition tests, liver function tests, urinalysis, electrocardiograms, fundus examinations, and chest X-rays. The medical examination equipment includes, for example, height/weight scales, blood pressure monitors, blood testing equipment, electrocardiographs, X-ray imaging equipment, ultrasound equipment, computed tomography (CT) equipment, and magnetic resonance imaging (MRI) equipment. The medical examination vehicle 12 is connected to the network 11 via a mobile communication network. The medical examination vehicle 12 is driven manually, but a portion of driving may be automated. The medical examination vehicle 12 is any type of automobile such as a gasoline vehicle, a Battery Electric Vehicle (BEV), a Hybrid Electric Vehicle (HEV), a Plug-in Hybrid Electric Vehicle (PHEV), or a Fuel Cell Electric Vehicle (FCEV).

The terminal apparatus 13 is an information processing apparatus used by the patient who undergoes a medical examination by the medical examination vehicle 12. Examples of the terminal apparatus 13 include a smartphone, a tablet terminal, and a personal computer (PC).

The network 11 is the Internet, for example, but may also be an ad-hoc network, a LAN, a Metropolitan Area Network (MAN), other networks, or a combination of two or more thereof.

In the present embodiment, the server apparatus 10 assists the patient using the terminal apparatus 13 to undergo a medical examination in the medical examination vehicle 12. The server apparatus 10 receives information for identifying a patient from a terminal apparatus 13 and outputs, on a condition that a total examination time is equal to or less than a travel time for a travel route of the patient, information to one or more medical examination vehicles 12 that each provide a medical examination for one or more examination items on which the patient has not yet been examined, the information being for causing the one or more medical examination vehicles 12 to travel the travel route. The medical examination vehicle 12 travels based on the information received from the server apparatus 10 and allows the patient to board. The patient can undergo a medical examination for the examination items provided by the medical examination vehicle 12 while traveling in the medical examination vehicle 12. The patient can transfer to another medical examination vehicle 12 while on the travel route. Even in a case in which the number of examination items that can be provided by each medical examination vehicle 12 is limited, the patient can make effective use of travel time and undergo a series of examination items by transferring between multiple medical examination vehicles 12 and undergoing a medical examination in each medical examination vehicle 12. In other words, convenience for patients can be improved.

Figure 2:
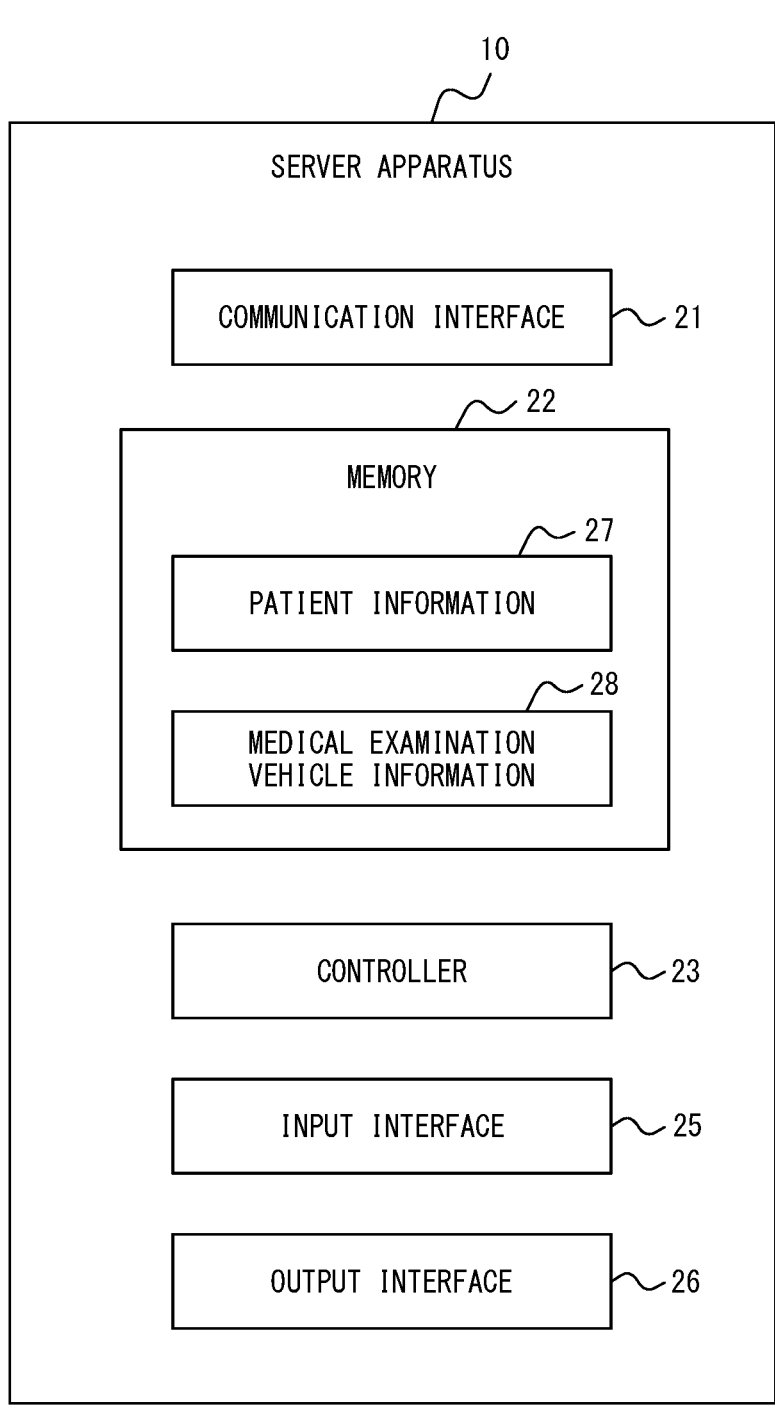
FIG. 2 is a diagram illustrating an example configuration of a server apparatus.

FIG. 2 illustrates an example configuration of the server apparatus 10. The server apparatus 10 includes a communication interface 21, a memory 22, a controller 23, an input interface 25, and an output interface 26. The server apparatus 10 is, for example, a single computer. The server apparatus 10 may be two or more server computers that are communicably connected to each other and operate in cooperation. In this case, the configuration illustrated in FIG. 2 is arranged among two or more server computers as appropriate.

The communication interface 21 includes one or more interfaces for communication. The interface for communication is, for example, a LAN interface. The communication interface 21 receives information to be used for the operations of the server apparatus 10 and transmits information obtained by the operations of the server apparatus 10. The server apparatus 10 is connected to the network 11 by the communication interface 21 and communicates information with the medical examination vehicle 12 or the terminal apparatus 13 via the network 11.

The memory 22 includes, for example, one or more semiconductor memories, one or more magnetic memories, one or more optical memories, or a combination of at least two of these types, to function as main memory, auxiliary memory, or cache memory. The semiconductor memory is, for example, Random Access Memory (RAM) or Read Only Memory (ROM). The RAM is, for example, Static RAM (SRAM) or Dynamic RAM (DRAM). The ROM is, for example, Electrically Erasable Programmable ROM (EEPROM). The memory 22 stores information to be used for the operations of the server apparatus 10 and information obtained by the operations of the server apparatus 10. The memory 22 stores patient information 27 and medical examination vehicle information 28. The patient information 27 includes, for each patient, identification information, information on the medical examination history, information on a travel plan, and the like. The medical examination history includes information such as examination items on which the patient has been examined and the date and time of examination. The travel plan includes information such as the departure point, estimated time of departure, destination, and estimated time of arrival at the destination. The medical examination vehicle information 28 includes identification information for each medical examination vehicle 12, examination items that can be provided, the test time required for testing of each examination item, and the like.

The controller 23 includes one or more processors, one or more dedicated circuits, or a combination thereof. The processor is a general purpose processor, such as a central processing unit (CPU), or a dedicated processor, such as a graphics processing unit (GPU), specialized for a particular process. The dedicated circuit is, for example, a field-programmable gate array (FPGA), an application specific integrated circuit (ASIC), or the like. The controller 23 executes information processing related to operations of the server apparatus 10 while controlling components of the server apparatus 10.

The input interface 25 includes one or more interfaces for input. The interface for input is, for example, a physical key, a capacitive key, a pointing device, a touch screen integrally provided with a display, or a microphone that receives audio input. The input interface 25 accepts operations to input information used for operation of the server apparatus 10 and transmits the inputted information to the controller 23.

The output interface 26 includes one or more interfaces for output. The interface for output is, for example, a display or a speaker. The display is, for example, a Liquid Crystal Display (LCD) or an organic Electro Luminescent (EL) display. The output interface 26 outputs information obtained by the operations of the server apparatus 10.

The functions of the server apparatus 10 are realized by a processor included in the controller 23 executing a control program. The control program is a program for causing a computer to execute the processing of steps included in the operations of the server apparatus 10, thereby enabling the computer to realize the functions corresponding to the processing of the steps. That is, the control program is a program for causing a computer to function as the server apparatus 10. Some or all of the functions of the server apparatus 10 may be realized by a dedicated circuit included in the controller 23. The control program may be stored on a non-transitory recording/storage medium readable by the server apparatus 10 and be read from the medium by the server apparatus 10.

Figure 3:
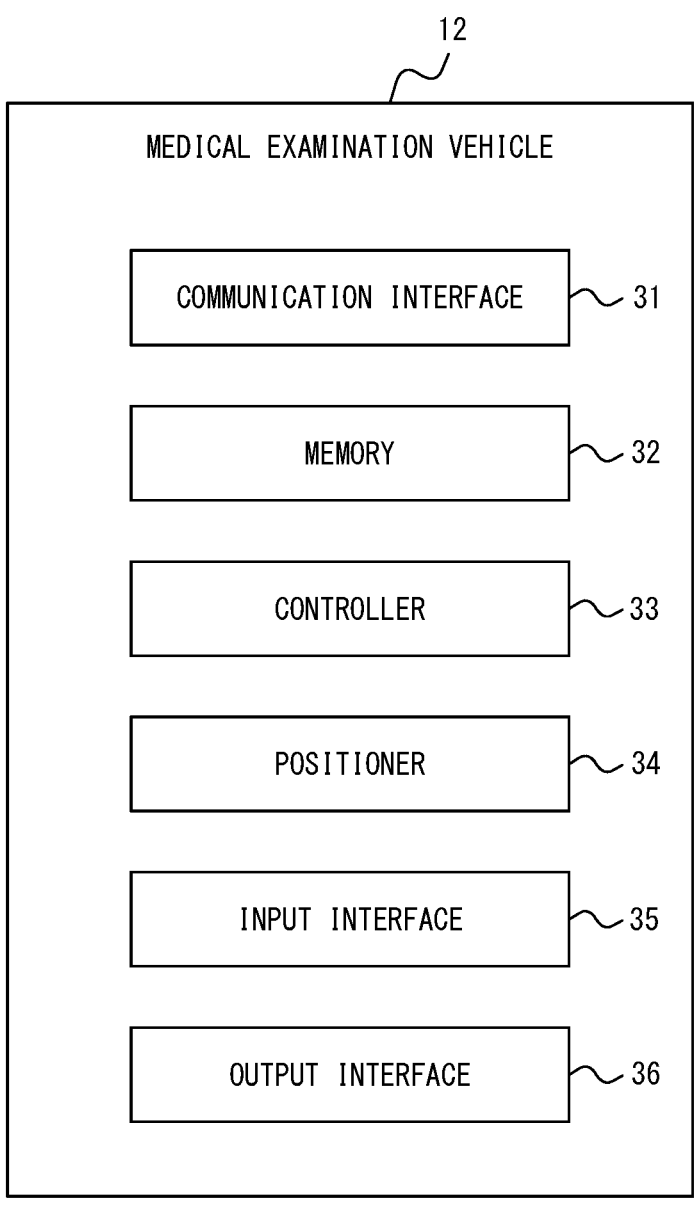
FIG. 3 is a diagram illustrating an example configuration of a medical examination vehicle.

FIG. 3 illustrates a configuration example of the medical examination vehicle 12. In addition to the medical examination equipment, the medical examination vehicle 12 includes a communication interface 31, a memory 32, a controller 33, a positioner 34, an input interface 35, and an output interface 36. These components may be configured as a single control apparatus, by two or more control apparatuses, or by other apparatuses, such as a control apparatus and a communication device. The control apparatus includes an electronic control unit (ECU), for example. The communication device includes a data communication module (DCM), for example. The control apparatus may be configured to include a personal computer, a tablet terminal, a smartphone terminal, a navigation apparatus, or the like. The components are communicably connected to each other, or to other devices and apparatuses in the medical examination vehicle 12, by an in-vehicle network compliant with standards such as a controller area network (CAN).

The communication interface 31 includes one or more interfaces for communication. Examples of the interface for communication include an interface corresponding to mobile communication standards, such as Long Term Evolution (LTE), 4th Generation (4G), or 5th Generation (5G). The communication interface 31 receives information to be used for the operations of the controller 33 and transmits information obtained by the operations of the controller 33. The controller 33 connects to the network 11 using the communication interface 31 through a mobile communication base station and communicates information with other apparatuses via the network 11.

The memory 32 includes, for example, one or more semiconductor memories, one or more magnetic memories, one or more optical memories, or a combination of at least two of these types. The semiconductor memory is, for example, RAM or ROM. The RAM is, for example, SRAM or DRAM. The ROM is, for example, EEPROM. The memory 32 functions as, for example, a main memory, an auxiliary memory, or a cache memory. The memory 32 stores information to be used for the operations of the controller 33 and information obtained by the operations of the controller 33.

The controller 33 includes one or more processors, one or more dedicated circuits, or a combination thereof. Examples of the processor include a general purpose processor such as a CPU and a dedicated processor dedicated to specific processing. The dedicated circuit is, for example, an FPGA or an ASIC. The controller 33 executes information processing pertaining to operations of the medical examination vehicle 12.

The positioner 34 includes one or more Global Navigation Satellite System (GNSS) receivers. The GNSS includes, for example, at least one of Global Positioning System (GPS), Quasi-Zenith Satellite System (QZSS), BeiDou, Global Navigation Satellite System (GLONASS), and Galileo. The positioner 34 acquires the positional information for the medical examination vehicle 12 and transmits the positional information to the controller 33.

The input interface 35 includes one or more interfaces for input. The interface for input is, for example, a physical key, a capacitive key, a pointing device, a touch screen integrally provided with a display, or a microphone that receives audio input. The interface for input may further include a camera or IC card reader that captures images or image codes. The input interface 35 accepts user operations to input information used for operation of the controller 33 and transmits the inputted information to the controller 33.

The output interface 36 includes one or more interfaces for output. The interface for output is, for example, a display or a speaker. The display is, for example, an LCD or an organic EL display. The output interface 36 outputs the information obtained by the operation of controller 33, for example, to the user.

The functions of the controller 33 are realized by a processor included in the controller 33 executing a control program. The control program is a program for causing a computer to execute the processing of steps included in operations of the controller 33, thereby enabling the computer to realize the functions corresponding to the processing of the steps. That is, the control program is a program for causing a computer to function as the controller 33. Some or all of the functions of the controller 33 may be realized by a dedicated circuit included in the controller 33. The controller 33 generates information for control of various mechanisms and apparatuses of the medical examination vehicle 12 and transmits the information for control to the control circuits of the various mechanisms and apparatuses to control the mechanisms and apparatuses.

Figure 4:
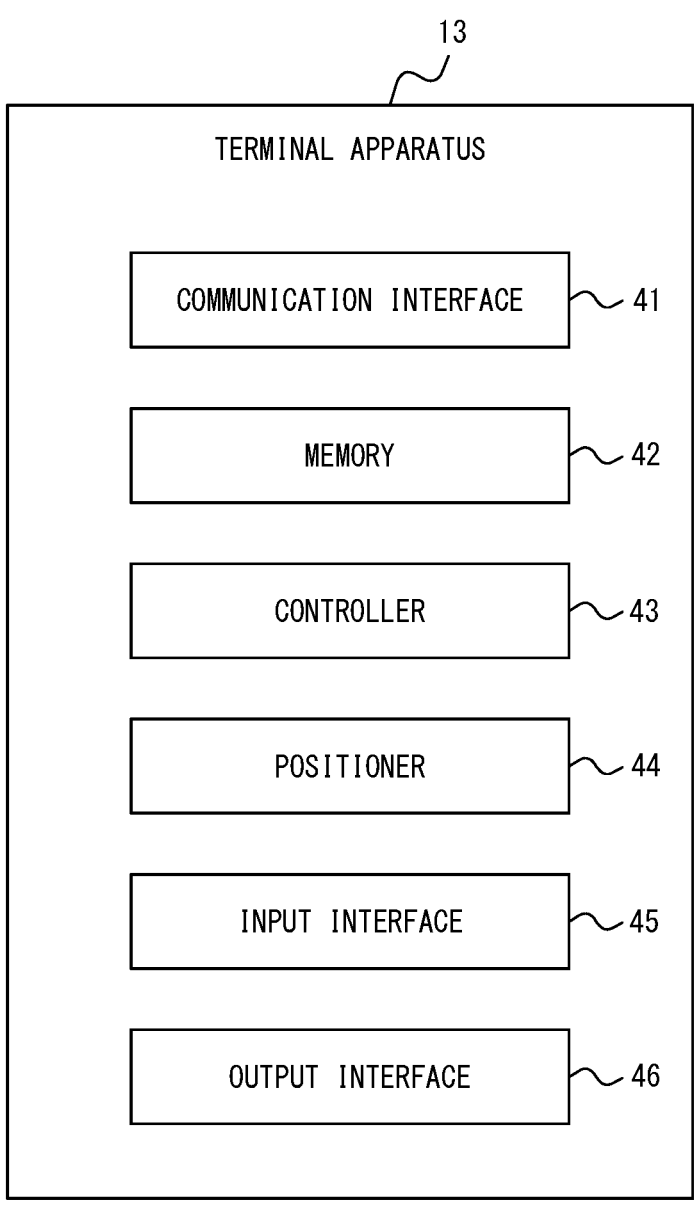
FIG. 4 is a diagram illustrating an example configuration of a terminal apparatus.

FIG. 4 is a diagram illustrating a configuration of the terminal apparatus 13. The terminal apparatus 13 is, for example, an information terminal apparatus such as a smartphone, a tablet terminal apparatus, or a personal computer. The terminal apparatus 13 includes a communication interface 41, a memory 42, a controller 43, a positioner 44, an input interface 45, and an output interface 46.

The communication interface 41 includes a communication module compliant with a wired or wireless LAN standard, a module compliant with a mobile communication standard such as LTE, 4G, or 5G, or the like. The terminal apparatus 13 connects to the network 11 via a nearby router apparatus or mobile communication base station using the communication interface 41 and communicates information with other apparatuses over the network 11.

The memory 42 includes, for example, one or more semiconductor memories, one or more magnetic memories, one or more optical memories, or a combination of at least two of these types. The semiconductor memory is, for example, RAM or ROM. The RAM is, for example, SRAM or DRAM. The ROM is, for example, EEPROM. The memory 42 functions as, for example, a main memory, an auxiliary memory, or a cache memory. The memory 42 stores information to be used for the operations of the controller 43 and information obtained by the operations of the controller 43.

The controller 43 has one or more general purpose processors such as CPUs or micro processing units (MPUs) or one or more dedicated processors that are dedicated to specific processing. Alternatively, the controller 43 may have one or more dedicated circuits such as FPGAs or ASICs. The controller 43 is configured to perform overall control of the operations of the terminal apparatus 13 by operating according to the control/processing programs or operating according to operation procedures implemented in the form of circuits. The controller 43 then transmits and receives various types of information to and from the server apparatus 10 and the like via the communication interface 41 and executes the operations according to the present embodiment.

The positioner 44 includes one or more GNSS receivers. GNSS includes, for example, GPS, QZSS, BeiDou, GLONASS, and/or Galileo. The positioner 44 acquires the positional information for the terminal apparatus 13 and transmits the positional information to the controller 43.

The input interface 45 includes one or more interfaces for input. The interface for input is, for example, a physical key, a capacitive key, a pointing device, a touch screen integrally provided with a display, or a microphone that receives audio input. The interface for input may further include a camera or IC card reader that captures images or image codes. The input interface 45 accepts operations for inputting information to be used in the operations of the controller 43 and transmits the inputted information to the controller 43.

The output interface 46 includes one or more interfaces for output. The interface for output is, for example, a display or a speaker. The display is, for example, an LCD or an organic EL display. The output interface 46 outputs information obtained by the operations of the controller 43.

The functions of the controller 43 are realized by a processor included in the controller 43 executing a control program. The control program is a program for causing the processor to function as the controller 43. Some or all of the functions of the controller 43 may be realized by a dedicated circuit included in the controller 43.

Operations of the information processing system 1 are now described with reference to FIG. 5.

Figure 5:
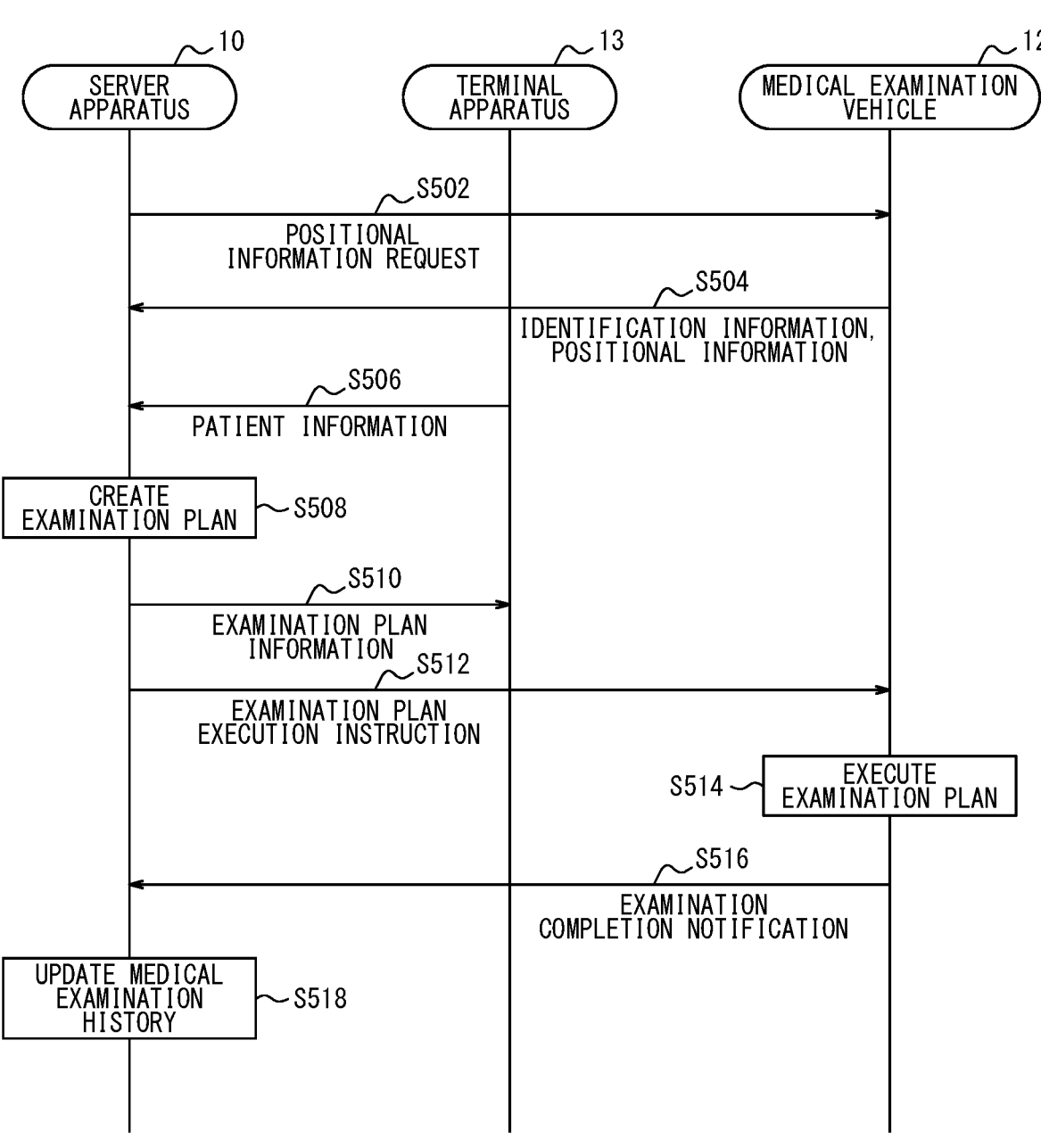
FIG. 5 is a sequence diagram illustrating an operation example of the information processing system.

FIG. 5 is a sequence diagram to illustrate the operating procedures of the information processing system 1 in the present embodiment. FIG. 5 illustrates the steps in the coordinated operation of the server apparatus 10, the medical examination vehicle 12, and the terminal apparatus 13. Although an example of coordinated operation of the server apparatus 10 and the terminal apparatus 13 is illustrated here for the case of a single medical examination vehicle 12, the operation example illustrated here also applies to each medical examination vehicle 12 in the case of a plurality of medical examination vehicles 12. The steps pertaining to the various information processing by the server apparatus 10, the medical examination vehicle 12, and the terminal apparatus 13 in FIG. 5 are performed by the respective controllers 23, 33, 43. The steps pertaining to transmitting and receiving various types of information to and from the server apparatus 10, the medical examination vehicle 12, and the terminal apparatus 13 are performed by the respective controllers 23, 33, 43 transmitting and receiving information to and from each other via the respective communication interfaces 21, 31, 41. In the server apparatus 10, the medical examination vehicle 12, and the terminal apparatus 13, the respective controllers 23, 33, 43 appropriately store the information that is transmitted and received in the respective memories 22, 32, 42. Furthermore, the controllers 23, 33, 43 accept input of various information by the respective input interfaces 35, 45 and output various information by the respective output interfaces 36, 46.

In step S502, the server apparatus 10 transmits information for requesting positional information to each medical examination vehicle 12. The positional information is information indicating the current position of each medical examination vehicle 12.

In step S504, each medical examination vehicle 12 transmits its own positional information to the server apparatus 10. The positional information is derived by the controller 33 using information acquired by the positioner 34.

In step S506, the terminal apparatus 13 transmits patient information to the server apparatus 10. The patient uses the terminal apparatus 13 to access a website operated by a medical examination provider on the server apparatus 10, for example, and transmits various information to the server apparatus 10, such as identification information and travel plans. The identification information of the patient is transmitted to the server apparatus 10 once at the time of user registration, for example, and is stored on the server apparatus 10 as part of the patient information 27. The travel plan and the like are transmitted from the terminal apparatus 13 to the server apparatus 10 at any appropriate time by the patient and are updated on the server apparatus 10 as needed. The terminal apparatus 13 may transmit the positional information on the current position to the server apparatus 10, and the server apparatus 10 may use the current position of the terminal apparatus 13 as the departure point for the initial travel route.

In step S508, the server apparatus 10 creates an examination plan. The examination plan includes information such as the travel route from the departure point to the destination in the patient's travel plan (hereinafter referred to as the initial travel route), the examination items to be provided to the patient during travel on the travel route, the medical examination vehicles 12 that provide the examination items, the travel route allocated to each medical examination vehicle 12 along the initial travel route (hereinafter referred to as the assigned travel route), the travel route from the current location of each medical examination vehicle 12 to the start point of the assigned travel route, the travel speed and estimated time of arrival, the travel speed from the start point to the end point of the assigned travel route, and the estimated time of arrival at the end point. When a plurality of medical examinations vehicles 12 are assigned to the initial travel route, the end point of the assigned travel route for one medical examination vehicle 12, i.e., the start point of the assigned travel route for another medical examination vehicle 12, corresponds to the transfer point for the patient to transfer between medical examination vehicles 12.

Figure 6:
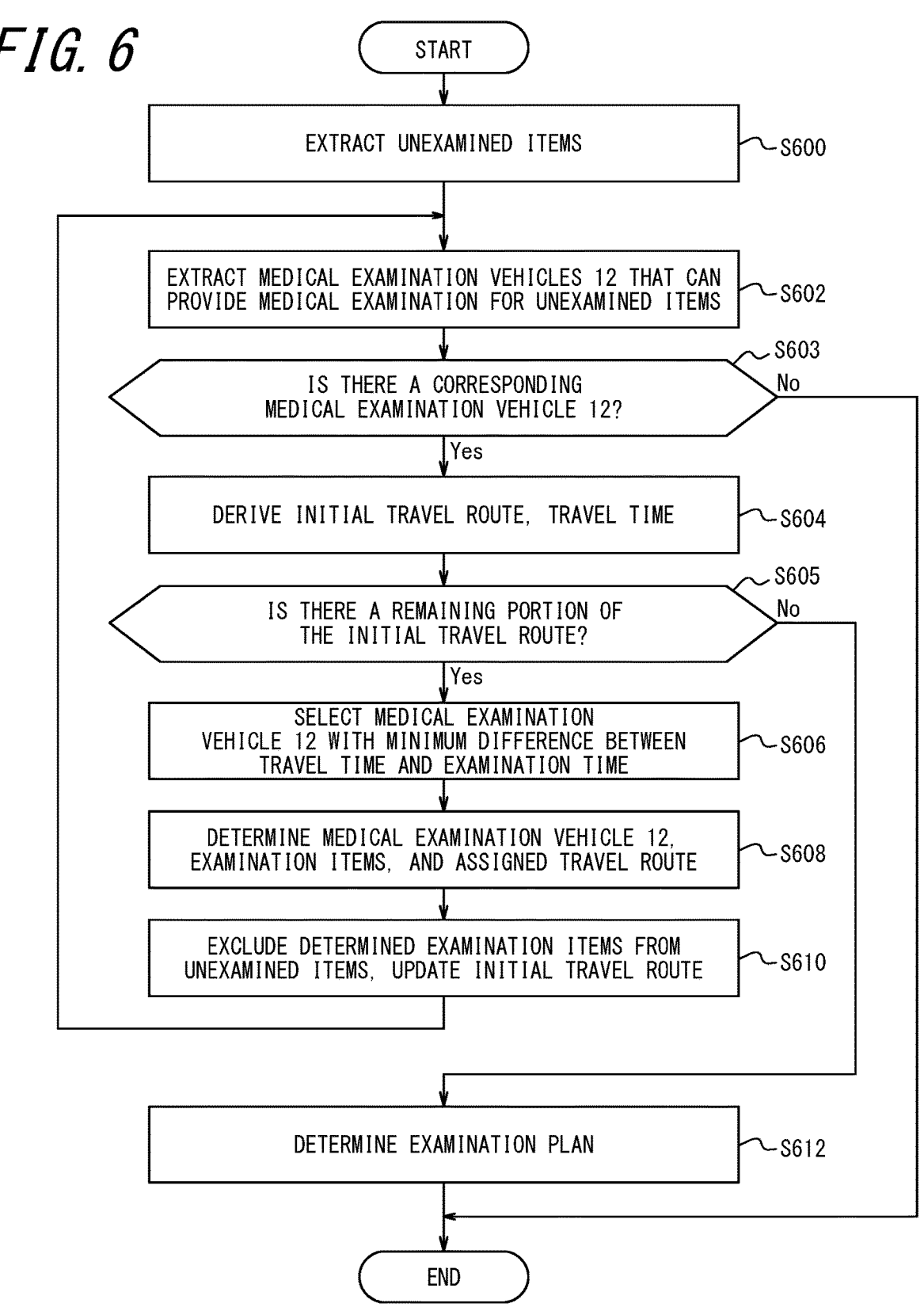
FIG. 6 is a flowchart illustrating an operation example of the server apparatus.

FIG. 6 is a flowchart illustrating a detailed example of the procedures in step S508.

In step S600, the controller 23 of the server apparatus 10 identifies the examination items on which the patient has not yet been examined (hereinafter referred to as unexamined items). The controller 23 refers to the medical examination history associated with the identification information for the patient and extracts, for example, examination items with no examination history in the current year as unexamined items.

In step S602, the controller 23 extracts medical examination vehicles 12 that can provide a medical examination for the unexamined items. With reference to the medical examination vehicle information 28, the controller 23 extracts medical examination vehicles 12 that can provide a medical examination for the unexamined items extracted in step S600. In a case in which the corresponding medical examination vehicles 12 are extracted (Yes in step S603), the controller 23 proceeds to step S604, whereas otherwise (No in step S603), the process is terminated.

In step S604, the controller 23 derives the initial travel route and the corresponding travel time. As an initial setting, the controller 23 derives an initial travel route from the departure point to the destination identified by the travel plan. In a case in which the initial travel route is updated after step S608 described below, the travel route to the new departure point on the way from the departure point to the destination is derived as the updated initial travel route. Map information and any appropriate search algorithm are used to derive the initial travel route. The controller 23 also calculates, for example, the travel time for the initial travel route in the case of the medical examination vehicle 12 traveling at a legal speed. In a case in which there is a remaining portion of the initial travel route to be traveled by the medical examination vehicle 12 (Yes in step S605), the controller 23 proceeds to step S606, whereas otherwise (No in step S605), the controller 23 proceeds to step S612.

In step S606, the controller 23 selects the medical examination vehicle 12, from among the extracted medical examination vehicles 12, such that the difference between the travel time for the initial travel route and the examination time for each medical examination vehicle 12 is minimized. The controller 23 may use the positional information for each medical examination vehicle 12 to select the medical examination vehicle 12 on the condition that the medical examination vehicle 12 is located within an appropriate reference distance range from the departure point. The reference distance range can, for example, be determined in range of several hundred meters to several kilometers, depending on the length of time between the current time and the scheduled departure time.

In step S608, the controller 23 determines the selected medical examination vehicle 12, the examination items to be provided by that medical examination vehicle 12, and the assigned travel route for that medical examination vehicle 12. The assigned travel route is derived and determined as the portion of the initial travel route that the medical examination vehicle 12 can travel during the examination time.

In step S610, the controller 23 excludes the determined examination items from the unexamined items extracted in step S600 and updates the initial travel route. By exclusion of the assigned travel route determined in step S608 from the initial travel route, the remaining route is determined as the updated initial travel route. The controller 23 then returns to step S602.

Steps S602 through S608 are repeated until no portion of the initial travel route remains, so as to select and determine additional medical examination vehicles 12 that can provide a medical examination for unexamined items within the travel time of the initial travel route. In other words, at this time an additional medical examination vehicle 12 is selected on the condition that the examination time corresponding to the additional medical examination vehicle 12 is equal to or less than the difference between the examination time corresponding to the already determined medical examination vehicles 12 and the travel time. Thus, one or more medical examination vehicles 12, which satisfy the condition of the total examination time being equal to or less than the travel time for the initial travel route, and the corresponding examination items are determined.

In step S612, the controller 23 determines the examination plan. The examination plan includes one or more medical examination vehicles 12 and the examination items provided by each one, the assigned travel route for each medical examination vehicle, the scheduled departure time at the start point and the scheduled arrival time at the end point of each assigned travel route, and the like. In a case in which a plurality of medical examination vehicles 12 is determined, the transfer point from one medical examination vehicle 12 to another medical examination vehicle 12 is included in the examination plan.

Returning to FIG. 5, in step S510, the server apparatus 10 transmits examination plan information to the terminal apparatus 13. The terminal apparatus 13 displays the examination plan to present the examination plan to the patient, so that the patient can confirm the examination plan. The patient can travel to the departure point (the start point of the assigned travel route of the first medical examination vehicle 12) to board the medical examination vehicle 12. Alternatively, the patient may wait for the medical examination vehicle 12 at the patient's current position. When the examination plan is created in step S508, in a case in which there are no medical examination vehicles 12 that can provide a medical examination, information indicating that the examination plan cannot be executed is transmitted from the server apparatus 10 to the terminal apparatus 13, and steps S512 and thereafter are omitted.

In step S512, the server apparatus 10 transmits an instruction to execute the examination plan to each target medical examination vehicle 12. In other words, information for causing the medical examination vehicle 12 to travel to the start point of the assigned travel route for the patient to board is transmitted to the medical examination vehicle 12.

In step S514, the medical examination vehicle 12 executes the examination plan. The medical examination vehicle 12 starts traveling according to the examination plan, and when the patient boards at the start point of the assigned travel route, the medical examination is provided in the moving medical examination vehicle 12. The medical examination is provided, for example, through the use of the medical examination equipment in the medical examination vehicle 12 by medical personnel on board the medical examination vehicle 12. Alternatively, a portion or all of the medical examination may be performed by automated machines. The medical examination is completed by the time the medical examination vehicle 12 arrives at the end point of the assigned travel route. In a case in which the next medical examination vehicle 12 has been assigned, the patient can transfer to the next medical examination vehicle 12 at the transfer point and undergo a medical examination in that medical examination vehicle 12.

In step S516, the medical examination vehicle 12 transmits an examination completion notification to the server apparatus 10.

In step S518, the server apparatus 10 updates the medical examination history in the patient information 27 in response to the examination completion notification. The server apparatus 10 updates the examination date and time of the examination items for which the medical examination was completed. In a case in which a plurality of medical examination vehicles 12 is assigned, the server apparatus 10 updates the medical examination history based on the examination completion notification for each medical examination vehicle 12.

By a plurality of medical examination vehicles 12 respectively performing steps S514 and S516, the patient can undergo medical examinations while transferring between medical examination vehicles 12.

According to the above-described procedures, even in a case in which the number of examination items that can be provided by each medical examination vehicle 12 is limited, the patient can make effective use of travel time and undergo a series of examination items by transferring between multiple medical examination vehicles 12 and undergoing a medical examination in each medical examination vehicle 12. In other words, convenience for patients can be improved.

In the above embodiment, a processing/control program that specifies operations of the medical examination vehicle 12 and the terminal apparatus 13 may be stored in the memory 22 of the server apparatus 10 or in the memory of another server apparatus and be downloaded onto each apparatus via the network 11. The processing/control program may also be stored on a non-transitory recording/ storage medium readable by each apparatus, and each apparatus may read the program from the medium.

While embodiments have been described with reference to the drawings and examples, it should be noted that various modifications and revisions may be implemented by those skilled in the art based on the present disclosure. Accordingly, such modifications and revisions are included within the scope of the present disclosure. For example, functions or the like included in each means, each step, or the like can be rearranged without logical inconsistency, and a plurality of means, steps, or the like can be combined into one or divided.

Examples of some embodiments of the present disclosure are described below. However, it should be noted that the embodiments of the present disclosure are not limited to these examples.

[Appendix 1] A server apparatus comprising:

a communication interface; and a controller configured to communicate using the communication interface, wherein the controller is configured to receive information for identifying a patient from a terminal apparatus and output, on a condition that a total examination time is equal to or less than a travel time for a travel route of the patient, information to one or more medical examination vehicles that each provide a medical examination for one or more examination items on which the patient has not yet been examined, the information being for causing the one or more medical examination vehicles to travel the travel route.

[Appendix 2] The server apparatus according to appendix 1, wherein the controller is configured to receive information for identifying the travel route from the terminal apparatus and transmit information, to a first medical examination vehicle, for causing the first medical examination vehicle to travel to a start point of the travel route for the patient to board.

[Appendix 3] The server apparatus according to appendix 2, wherein the controller is configured to transmit information, to the first medical examination vehicle, for causing the first medical examination vehicle to travel to a transfer point with a second medical examination vehicle, and transmit information, to the second medical examination vehicle, for causing the second medical examination vehicle to travel to the transfer point for the patient to board.

[Appendix 4] The server apparatus according to appendix 3, wherein the controller is configured to select the second medical examination vehicle on a condition that an examination time corresponding to the second medical examination vehicle is equal to or less than a difference between an examination time corresponding to the first medical examination vehicle and the travel time.

[Appendix 5] The server apparatus according to any one of appendices 1 to 4, further comprising a memory configured to store a medical examination history for each patient, wherein the controller is configured to identify one or more examination items on which the patient has not yet been examined based on the information received from the terminal apparatus and the medical examination history stored in the memory.

[Appendix 6] The server apparatus according to any one of appendices 1 to 5, further comprising a memory configured to store information on examination items and an examination time for each medical examination vehicle, wherein the controller is configured to select one or more medical examination vehicles that each provide a medical examination for one or more examination items on which the patient has not yet been examined based on the information stored in the memory.

[Appendix 7] The server apparatus according to any one of appendices 1 to 6, further comprising a memory configured to store information on a travel plan for each patient, wherein the controller is configured to derive a travel route for the patient based on the information received from the terminal apparatus and the information stored in the memory.

[Appendix 8] A system comprising one or more medical examination vehicles and a server apparatus configured to communicate with each other, wherein the server apparatus is configured to receive information for identifying a patient from a terminal apparatus and output, on a condition that a total examination time is equal to or less than a travel time for a travel route of the patient, information to the one or more medical examination vehicles that each provide a medical examination for one or more examination items on which the patient has not yet been examined, the information being for causing the one or more medical examination vehicles to travel the travel route, and the one or more medical examination vehicles are configured to travel the travel route based on the information from the server apparatus.

[Appendix 9] The system according to appendix 8, wherein the server apparatus is configured to receive information for identifying the travel route from the terminal apparatus and transmit information, to a first medical examination vehicle, for causing the first medical examination vehicle to travel to a start point of the travel route for the patient to board.

[Appendix 10] The system according to appendix 9, wherein the server apparatus is configured to transmit information, to the first medical examination vehicle, for causing the first medical examination vehicle to travel to a transfer point with a second medical examination vehicle, and transmit information, to the second medical examination vehicle, for causing the second medical examination vehicle to travel to the transfer point for the patient to board.

[Appendix 11] The system according to appendix 10, wherein the server apparatus is configured to select the second medical examination vehicle on a condition that an examination time corresponding to the second medical examination vehicle is equal to or less than a difference between an examination time corresponding to the first medical examination vehicle and the travel time.

[Appendix 12] The system according to any one of appendices 8 to 11, wherein the server apparatus further comprises a memory configured to store a medical examination history for each patient, and the server apparatus is configured to identify one or more examination items on which the patient has not yet been examined based on the information received from the terminal apparatus and the medical examination history stored in the memory.

[Appendix 13] The system according to any one of appendices 8 to 12, wherein the server apparatus further comprises a memory configured to store information on examination items and an examination time for each medical examination vehicle, and the server apparatus is configured to select one or more medical examination vehicles that each provide a medical examination for one or more examination items on which the patient has not yet been examined based on the information stored in the memory.

[Appendix 14] The system according to any one of appendices 8 to 13, wherein the server apparatus further comprises a memory configured to store information on a travel plan for each patient, and the server apparatus is configured to derive a travel route for the patient based on the information received from the terminal apparatus and the information stored in the memory.

[Appendix 15] An operating method of a system comprising one or more medical examination vehicles and a server apparatus configured to communicate with each other, the operating method comprising:

receiving, by the server apparatus, information for identifying a patient from a terminal apparatus and outputting, on a condition that a total examination time is equal to or less than a travel time for a travel route of the patient, information to the one or more medical examination vehicles that each provide a medical examination for one or more examination items on which the patient has not yet been examined, the information being for causing the one or more medical examination vehicles to travel the travel route; and traveling, by the one or more medical examination vehicles, the travel route based on the information from the server apparatus.

[Appendix 16] The operating method according to appendix 15, wherein the server apparatus receives information for identifying the travel route from the terminal apparatus and transmits information, to a first medical examination vehicle, for causing the first medical examination vehicle to travel to a start point of the travel route for the patient to board.

[Appendix 17] The operating method according to appendix 16, wherein the server apparatus transmits information, to the first medical examination vehicle, for causing the first medical examination vehicle to travel to a transfer point with a second medical examination vehicle, and transmits information, to the second medical examination vehicle, for causing the second medical examination vehicle to travel to the transfer point for the patient to board.

[Appendix 18] The operating method according to appendix 17, wherein the server apparatus selects the second medical examination vehicle on a condition that an examination time corresponding to the second medical examination vehicle is equal to or less than a difference between an examination time corresponding to the first medical examination vehicle and the travel time.

[Appendix 19] The operating method according to any one of appendices 15 to 18, wherein the server apparatus further comprises a memory configured to store a medical examination history for each patient and identifies one or more examination items on which the patient has not yet been examined based on the information received from the terminal apparatus and the medical examination history stored in the memory.

[Appendix 20] The operating method according to any one of appendices 15 to 19, wherein the server apparatus further comprises a memory configured to store information on examination items and an examination time for each medical examination vehicle and selects one or more medical examination vehicles that each provide a medical examination for one or more examination items on which the patient has not yet been examined based on the information stored in the memory.

The invention claimed is:

1. A server apparatus comprising:
a communication interface; and
a controller configured to communicate using the communication interface, wherein
the controller is configured to
receive first information for identifying a patient and second information for identifying a travel route of the patient from a terminal apparatus of the patient,
transmit, on a condition that a total examination time for the patient is equal to or less than a travel time for the travel route of the patient, to one or more medical examination vehicles that each provide an automated medical examination for one or more examination items on which the patient has not yet been examined, third information causing the one or more medical examination vehicles to travel the travel route, transmit, to a first medical examination vehicle among the one or more medical examination vehicles, fourth information causing the first medical examination vehicle to travel to a start point of the travel route for the patient to board the first medical examination vehicle and then travel to a first transfer point with a second medical examination vehicle among the one or more medical examination vehicles, wherein the first medical examination vehicle provides the patient with a first automated medical examination for a first examination item among the one or more examination items while the first medical examination vehicle travels from the start point to the first transfer point, and transmit, to the second medical examination vehicle, fifth information causing the second medical examination vehicle to travel to the first transfer point for the patient to board the second medical examination vehicle and then travel to a second transfer point or an end point of the travel route, wherein the second medical examination vehicle provides the patient with a second automated medical examination for a second examination item among the one or more examination items while the second medical examination vehicle travels from the first transfer point to the second transfer point or the end point.

2. The server apparatus according to claim 1, further comprising a memory configured to store a medical examination history for each patient, wherein
the controller is further configured to identify the one or more examination items based on the first information received from the terminal apparatus and the medical examination history stored in the memory.

3. The server apparatus according to claim 2, wherein
the memory is further configured to store sixth information on examination items and an examination time for each medical examination vehicle, and
the controller is further configured to select the one or more medical examination vehicles based on the sixth information stored in the memory.

4. The server apparatus according to claim 1, wherein the controller is further configured to select, as the first medical examination vehicle, from among the one or more examination vehicles, a medical examination vehicle for which a difference between the travel time for the travel route of the patient and an examination time for the medical examination vehicle is minimized.

5. The server apparatus according to claim 1, wherein the controller is further configured to select, as the first medical examination vehicle, from among the one or more examination vehicles, a medical examination vehicle that is located within a predetermined distance range from the start point of the travel route.

6. The server apparatus according to claim 1, wherein the controller is further configured to select the second medical examination vehicle on a condition that a second examination time for the second automated medical examination is equal to or less than a difference between a first examination time for the first automated medical examination vehicle and the travel time.

7. A system comprising one or more medical examination vehicles and a server apparatus configured to communicate with each other, wherein the server apparatus is configured to receive first information for identifying a patient and second information for identifying a travel route of the patient from a terminal apparatus of the patient, transmit, on a condition that a total examination time for the patient is equal to or less than a travel time for the travel route of the patient, to the one or more medical examination vehicles that each provide an automated medical examination for one or more examination items on which the patient has not yet been examined, third information causing the one or more medical examination vehicles to travel the travel route, transmit, to a first medical examination vehicle among the one or more medical examination vehicles, fourth information causing the first medical examination vehicle to travel to a start point of the travel route for the patient to board the first medical examination vehicle and then travel to a first transfer point with a second medical examination vehicle among the one or more medical examination vehicles, wherein the first medical examination vehicle provides the patient with a first automated medical examination for a first examination item among the one or more examination items while the first medical examination vehicle travels from the start point to the first transfer point, and transmit, to the second medical examination vehicle, fifth information causing the second medical examination vehicle to travel to the first transfer point for the patient to board the second medical examination vehicle and then travel to a second transfer point or an end point of the travel route, wherein the second medical examination vehicle provides the patient with a second automated medical examination for a second examination item among the one or more examination items while the second medical examination vehicle travels from the first transfer point to the second transfer point or the end point.

8. The system according to claim 7, wherein the server apparatus further comprises a memory configured to store a medical examination history for each patient, and the server apparatus is further configured to identify the one or more examination items based on the first information received from the terminal apparatus and the medical examination history stored in the memory.

9. The system according to claim 8, wherein the server apparatus is further configured to store, in the memory, sixth information on examination items and an examination time for each medical examination vehicle, and select the one or more medical examination vehicles based on the sixth information stored in the memory.

10. The system according to claim 7, the server apparatus is further configured to select, as the first medical examination vehicle, from among the one or more examination vehicles, a medical examination vehicle for which a difference between the travel time for the travel route of the patient and an examination time for the medical examination vehicle is minimized.

11. The system according to claim 7, the server apparatus is further configured to select, as the first medical examination vehicle, from among the one or more examination vehicles, a medical examination vehicle that is located within a predetermined distance range from the start point of the travel route.

12. The system according to claim 7, wherein the server apparatus is further configured to select the second medical examination vehicle on a condition that a second examination time for the second automated medical examination is equal to or less than a difference between a first examination time for the first automated medical examination and the travel time.

13. An operating method of a server apparatus, the operating method comprising:

receiving, first information for identifying a patient and second information for identifying a travel route of the patient from a terminal apparatus of the patient;

transmitting, on a condition that a total examination time for the patient is equal to or less than a travel time for the travel route of the patient, to one or more medical examination vehicles that each provide an automated medical examination for one or more examination items on which the patient has not yet been examined, third information causing the one or more medical examination vehicles to travel the travel route;

transmitting, to a first medical examination vehicle among the one or more medical examination vehicles, fourth information causing the first medical examination vehicle to travel to a start point of the travel route for the patient to board the first medical examination vehicle and then travel to a first transfer point with a second medical examination vehicle among the one or more medical examination vehicles, wherein the first medical examination vehicle provides the patient with a first automated medical examination for a first examination item among the one or more examination items while the first medical examination vehicle travels from the start point to the first transfer point; and transmitting, to the second medical examination vehicle, fifth information causing the second medical examination vehicle to travel to the first transfer point for the patient to board the second medical examination vehicle and then travel to a second transfer point or an end point of the travel route, wherein the second medical examination vehicle provides the patient with a second automated medical examination for a second examination item among the one or more examination items while the second medical examination vehicle travels from the first transfer point to the second transfer point or the end point.

14. The operating method according to claim 13, further comprising:

storing a medical examination history for each patient in a memory of the server apparatus, and identifying the one or more examination items based on the first information received from the terminal apparatus and the medical examination history stored in the memory.

15. The operating method according to claim 14, further comprising:

storing, in the memory, sixth information on examination items and an examination time for each medical examination vehicle; and selecting the one or more medical examination vehicles based on the sixth information stored in the memory.

16. The operating method according to claim 13, further comprising:

selecting, as the first medical examination vehicle, from among the one or more examination vehicles, a medical examination vehicle for which a difference between the travel time for the travel route of the patient and an examination time for the medical examination vehicle is minimized.

17. The operating method according to claim 13, further comprising:

selecting, as the first medical examination vehicle, from among the one or more examination vehicles, a medical examination vehicle that is located within a predetermined distance range from the start point of the travel route.

18. The operating method according to claim 13, wherein the server apparatus further comprising:

selecting the second medical examination vehicle on a condition that a second examination time for the second automated medical examination is equal to or less than a difference between a first examination time for the first automated medical examination and the travel time.

* * * * *